United States Patent [19]

Gorski

[11] Patent Number: 5,489,306
[45] Date of Patent: Feb. 6, 1996

[54] GRADUATED POROSITY IMPLANT FOR FIBRO-OSSEOUS INTEGRATION

[76] Inventor: Jerrold M. Gorski, 137 William St., East Williston, N.Y. 11596

[21] Appl. No.: 367,598

[22] Filed: Jan. 3, 1995

[51] Int. Cl.⁶ .................... A61F 2/28; A61F 2/32
[52] U.S. Cl. ................ 623/16; 623/20; 623/23
[58] Field of Search .................. 623/16, 18, 20, 623/22, 23, 66

[56] References Cited

U.S. PATENT DOCUMENTS

| | | |
|---|---|---|
| 3,605,123 | 9/1971 | Hahn . |
| 3,808,606 | 5/1974 | Tronzo ................................. 623/16 |
| 3,855,638 | 12/1974 | Pilliar . |
| 3,906,550 | 9/1975 | Rostoker et al. . |
| 3,924,274 | 12/1975 | Heimke et al. . |
| 3,938,198 | 2/1976 | Kahn et al. . |
| 3,986,212 | 10/1976 | Sauer . |
| 3,987,499 | 10/1976 | Scharbach et al. . |
| 4,038,703 | 8/1977 | Bokros . |
| 4,064,567 | 12/1977 | Burstein et al. . |
| 4,129,470 | 12/1978 | Homsy ................................. 156/155 |
| 4,164,794 | 8/1979 | Spector et al. . |
| 4,206,516 | 6/1980 | Pilliar . |
| 4,351,069 | 9/1982 | Ballintyn et al. . |
| 4,362,681 | 12/1982 | Spector et al. .................. 264/112 |
| 4,536,894 | 8/1985 | Galante et al. .................. 623/22 |
| 4,542,539 | 9/1985 | Rowe, Jr. et al. .................. 623/16 |
| 4,553,272 | 11/1985 | Mears ................................. 623/1 |
| 4,599,085 | 7/1986 | Riess et al. .................. 623/16 |
| 4,636,219 | 1/1987 | Pratt et al. .................. 623/22 |
| 4,673,409 | 6/1987 | Van Kampen .................. 623/23 |
| 4,713,076 | 12/1987 | Draenert .................. 623/16 |
| 4,854,496 | 8/1989 | Bugle .................. 228/193 |
| 4,976,738 | 12/1990 | Frey et al. .................. 623/16 |
| 5,007,931 | 4/1991 | Smith .................. 623/23 |
| 5,201,766 | 4/1993 | Georgette .................. 623/16 |

*Primary Examiner*—David Isabella
*Attorney, Agent, or Firm*—Perman & Green

[57] ABSTRACT

A surgical prosthetic implant comprises a metallic substrate for insertion into the cavity of a long bone. A porous coating is provided on the substrate for encouraging bone and tissue ingrowth. The porous coating comprises at least a layer of particles of metallic material, which may be of the same material as the substrate. Graduated sized particles are used from proximal to distal ends of the implant creating graduated pore size between particles from proximal to distal ends. At a first zone at a proximal end of the substrate, the particles have a pore size in the range of approximately 325–425 microns for optimal bone-to-implant load transfer. At a second zone, advancing toward a distal end of the substrate, the particles have a pore size in the range of approximately 250–325 microns for significant bone ingrowth in a shorter time interval. At a third zone, the particles have a pore size in the range of approximately 175–250 microns for some bone ingrowth and some soft tissue ingrowth. At a fourth zone, the particles have a pore size in the range of approximately 100–175 microns for optimal soft tissue ingrowth with minimal bone ingrowth. At a fifth zone, the particles have a pore size of less than approximately 100 microns for optimal soft tissue ingrowth without permitting bone ingrowth. The porous coating may be of the same material as the substrate, which may be of stainless steel, titanium, titanium alloys, or chromium-cobalt alloys.

9 Claims, 2 Drawing Sheets

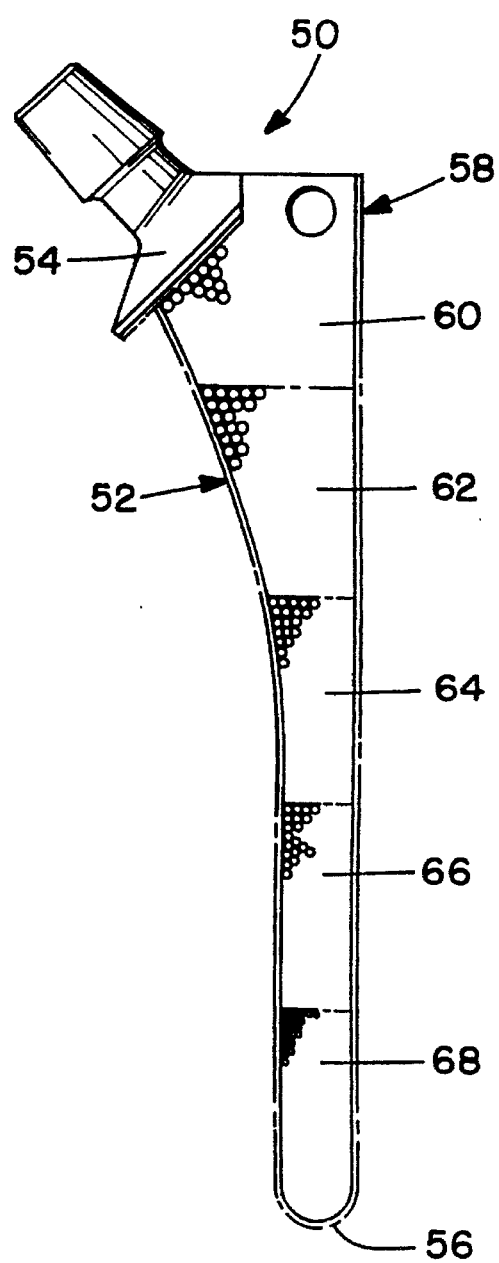
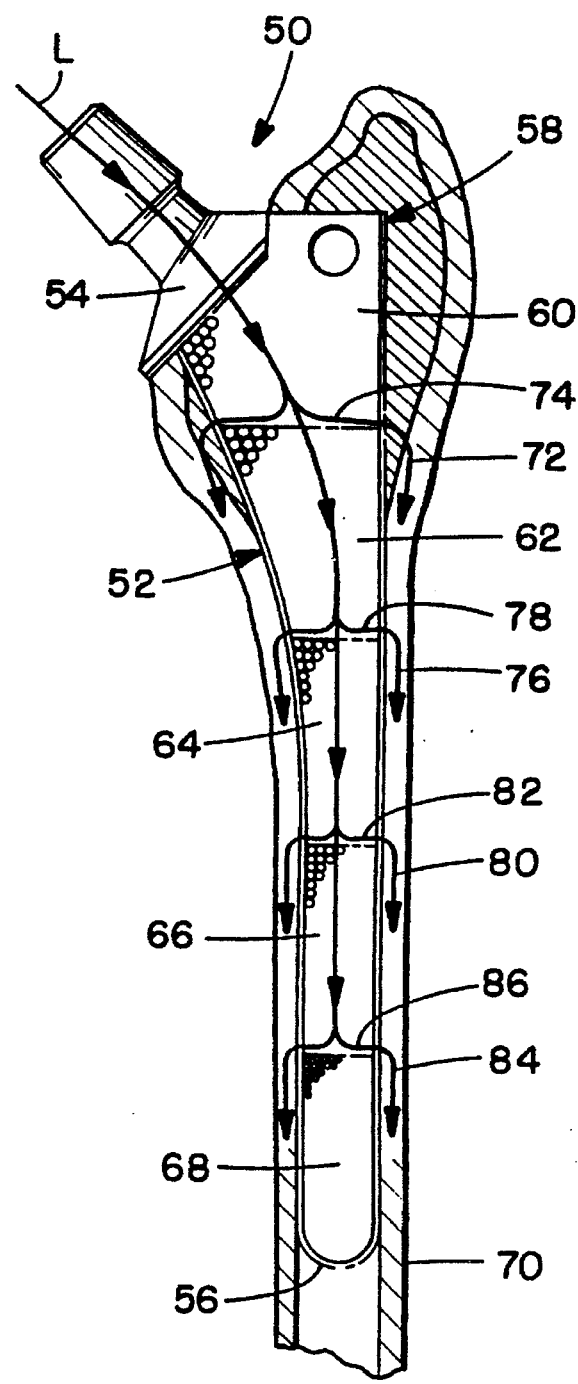
FIG. 3.
FIG. 4.

GRADUATED POROSITY IMPLANT FOR FIBRO-OSSEOUS INTEGRATION

BACKGROUND OF THE INVENTION

1. Field of the Invention

The present invention relates generally to prosthetic devices for replacing injured or diseased natural members and, more particularly, to such devices provided with porous surfaces for promoting bone ingrowth fixation.

Although the invention need not be so limited, it is disclosed in relation to a hip prosthesis adapted for insertion into the upper medullary canal in the femur of a patient. The hip prosthesis of this invention is of the type generally characterized as including a head or ball member, a shaft or stem member for insertion into the intramedullary canal, and a neck member connecting the head and stem. The prosthesis also includes a porous metal surface portion which provides for stabilization by bone ingrowth fixation without requiring any cement.

2. Description of the Prior Art

Prosthetic devices are used to partially or completely replace joints or bone segments in the skeletal structure of humans or animals. One of the major problems involved in the use of prosthetic devices is the attachment of the prosthetic implant to the adjacent bone. There are four general methods by means of which the device can be attached to the bone: (1) force fitting the implant into the medullary canal of the bone; (2) securing the implant in the bone with the aid of screws or pins; (3) bonding the implant by use of a plastic methyl methacrylic resin which is polymerized "in situ"; and (4) employing in conjunction with the implant a porous material into which bone may grow.

In modern times, the original hip replacement was described by Austin-Moore in *The Journal of Bone and Joint Surgery* in 1954. This original implant did not require cement and instead utilized large fenestrations in bone, the purpose of which was for bone ingrowth for stability. As this fenestration was too large to be ingrown in a practical time interval, the implant was commonly loose and moving within the bone marrow cavity. Clinical symptoms which this produced included pain and limping. Subsequently, after a variety of attempts at force-fitting the implant to the bone and attaching the implant to the bone, the next evolutionary improvement was the use of methyl-methacrylate cement for adhering the implant. Acrylic cements proved to be an improvement over the original cementless implants and were the state of the art for many years until follow-up results showed late loosening, bone loss, and a painful limp requiring very difficult revision surgery. Patients were restricted in terms of their activity level, and young people with arthritis were excluded from this surgery altogether.

A separate scientific enquiry based on the cementless biologically fixed Austin-Moore implant continued, even as cemented implants remained state of the art. A quantum improvement was the development of sintered porous bead technology. This type of porous surface was different than the original cementless implants of Austin-Moore, insofar as the pore size was microscopic and measured in microns, as opposed to the original fenestrations with a large pore size measured in terms of cubic centimeters. The smaller pore size allowed for more rapid and stable bone ingrowth. Originally, surgeons were incredulous that osteo-integration within these microscopic pores could occur. When this was proven, concern changed to various other potential concerns, including potential stress-shielding and optimal pore size for ingrowth. There were other concerns as to which metal alloy had optimal biocompatability. As time passed, various other proprietary techniques to develop porous surfaces were devised, and there were concerns about these, including plasma spray and fiber metals.

These latter concerns continue to this day with the latest proprietary technologies which involve the use of hydroxyappatite coatings. By no means, however, have these technologies assumed the mantle "state of the art."

The AML implant manufactured by DePuy, Inc. of Warsaw, Ind. has been studied in various forms, including different porous sizes, extent of porous coating, and the like. In fact, the AML implant may be the most carefully detailed and thoroughly studied total hip implant to date. It remains state of the art with the best clinical results for the longest time interval. The present invention seeks to improve on the successes of the AML implant and addresses some of the concerns that surgeons have about the short and long-term results of these most successful of the known implants.

It is only in recent years, then, that prosthetic devices have been provided with porous surfaces for bone ingrowth fixation. An excellent example of such a surface results from application of the proprietary porous metal coating of DePuy, Inc. of Warsaw, Ind., provided under the trademark "POROCOAT". Representative patents in this field include U.S. Pat. No. 3,605,123 to Hahn, U.S. Pat. No. 3,855,638 to Pilliar, U.S. Pat. No. 4,536,894 to Galante et al. and U.S. Pat. No. 4,854,496 to Bugle.

Prior cementless femoral components utilized one range of pore size. The extent of the porous coating was varied from 1/3 proximal coated (FIG. 1) to 4/5 proximal coated (FIG. 2) and even fully porous coated. Clinical investigation has determined that the more extensively porous-coated implants have the better result in terms of pain relief. It is, therefore, advantageous to maintain an extensively porous-coated implant in the new invention. It is not, however, a requirement to maintain bone ingrowth through this extensive porous implant. In fact, it is well known that it is difficult to design and obtain bone ingrowth through this extensive porous implant. In fact, it is well known that it is difficult to design and obtain bone ingrowth, at all. In some cases where there is no bone ingrowth, successful clinical results can be obtained entirely by a stable fibrous encapsulation. A priori, it is reasonable to assume that the naturally found normal physiologic loading of the proximal femur is the ideal objective to be obtained by an artificial implantation. A combination of maximizing bone ingrowth proximally with a diminishing amount of bone ingrowth through the middle zones of transition to a distal zone where fibrous tissue ingrowth is encouraged would serve to load the bone in a more physiological manner.

It was in light of the foregoing that the present invention was conceived and has now been reduced to practice.

SUMMARY OF THE INVENTION

According to the invention, then, a femoral component is fabricated with an extensive porous coating. The porous size tapers from proximal to distal zones, such that bone ingrowth is maximized proximally and tissue ingrowth distally, with a gradual transition from bone to tissue in between. Transfer of load from the implant to the proximal bone is maximized by increasing the volume of bone in the most proximal zone and lessening the volume of bone distally, wherein tissue ingrowth would occur exclusively.

Distally, tissue interposition would create a composite adhering the metal to bone, allowing stress transfer, mechanical stability and attenuation of the mismatch between these two dissimilar material's modulus of elasticity.

The problems overcome by this invention are twofold: (1) to eliminate thigh pain and (2) to prevent stress shielding occurring in femoral cementless osteo-integrated implants.

This is accomplished ideally by obtaining a harmonious equilibrium between host bone and artificial implant by simulation of normal anatomical, physiological and biomechanical forces in vivo.

After excessive activity, mid thigh pain may occur around a cementless implant. This is thought to be due to the fretting between dissimilar materials (bone and metal) possessing different moduli of elasticity. In short, with excess activity and loading the bone is bending around the smooth metal implant. This irritation results in a painful inflammatory response. Less relative motion and therefore less pain would result if a porous metal with adherent tissues is used.

Stress shielding of bone occurs as a natural response to non-physiological loading of bone. In short, bone is lost when it is not being loaded normally. Some surgeons believe that extensively porous coated implants like the DePuy AML will inevitably have proximal stress shielding because bone ingrowth and subsequent stress transfer will occur distally only. The proximal area atrophies because it is not being loaded normally—that is, it is stress shielded. Historically speaking, many designs limit the extent of porous coating to the proximal area only for fear of obtaining severe proximal stress shielding. Clinical results, however, show that implants with more extensive porous coatings have better clinical results and that stress shielding can occur even with proximal porous coatings only. Furthermore, surgeons have criticized implants with extensive porous coatings as nearly impossible to remove compared to only proximal ingrown implants. For these and other reasons to follow, an extensively porous coated implant that offers an optimal mix of bone and fibrous tissue integration would satisfy the need to obtain maximum stability and permanence in a more physiological simulation of normal loads.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 3 is a side elevation view of a femoral stem modified according to the invention; and FIG. 4 is a side elevation view, similar to FIG. 3, illustrating the modified femoral stem implanted in a femur and indicating the load paths resulting by reason of the invention.

DETAILED DESCRIPTION OF THE PREFERRED EMBODIMENT

Figure 1:
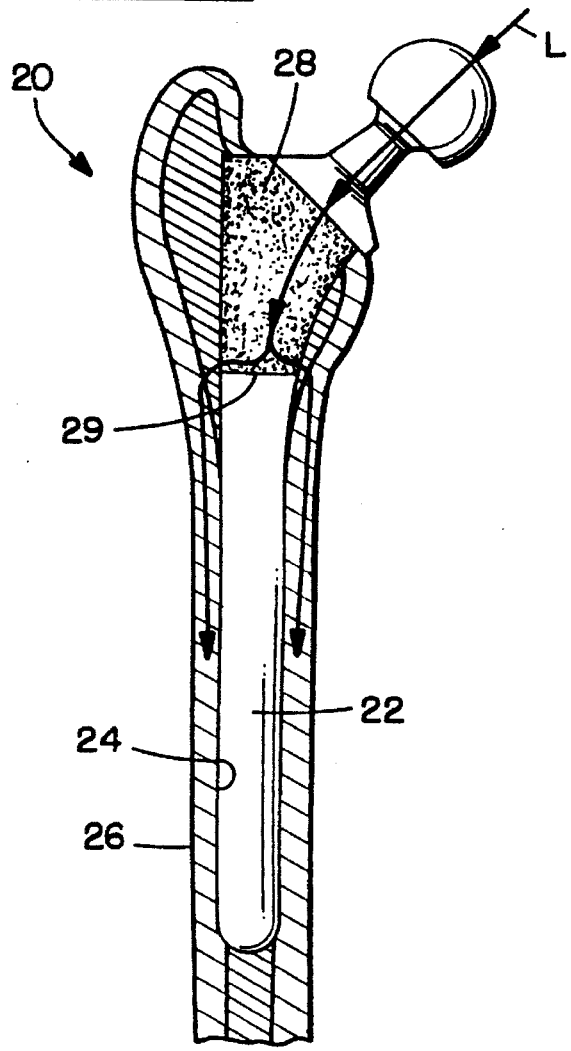
FIG. 1 is a side elevation view, certain parts being cut away and shown in section, of a conventional femoral stem with proximal fixation by means of a metallic porous coating.
Figure 2:
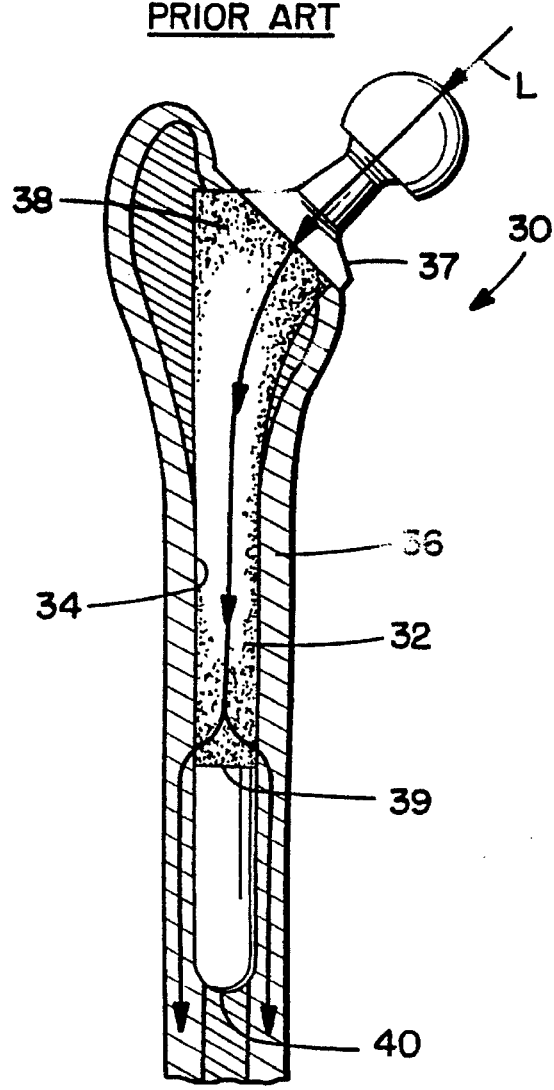
FIG. 2 is a side elevation view, similar to FIG. 1, of a conventional femoral stem with proximal and distal fixation by means of a metallic porous coating.

Turn now to the drawings and, initially, to FIGS. 1 and 2, both of which depict the prior art. In FIG. 1, a femoral prosthesis 20 is illustrated with a stem 22 implanted in the intramedullary canal 24 of a femur 26. A proximal region 28 is porous coated in a known manner, as by means of a porous metal coating, while the remainder of the stem from a transition line 29 down to its distal tip end remains unaltered, with a smooth outer surface.

As indicated with the aid of unnumbered arrows, a load L applied to the prosthesis 20 is transferred into the bone proximally and stress shielding is avoided. However, in the absence of soft or hard tissue ingrowth at the distal end of the prosthesis stem, there is relative motion between the stem and the bone. Such relative motion can undesirably result in thigh pain by the recipient and requires revision surgery. Experience with available implants of the prior art having porous surfaces limited to the proximal region reveals that patients experience more thigh pain than with implants having extensive porous surfaces. Also, attempts at using short stemmed implants alone have failed clinically. The graduated porosity concept is a method to minimize the problems inherent in longer stems.

In FIG. 2, a femoral prosthesis 30 is illustrated with a stem 32 implanted in the intramedullary canal 34 of a femur 36. Approximately four fifths of the stem extending from a shoulder 37 at a proximal region 38 down to a location 39 which is some distance in a proximal direction from a distal tip end 40 is porous coated in the manner of the proximal region 28 of the stem 22 of FIG. 1. As indicated with the aid of unnumbered arrows, a load L applied to the prosthesis 30 is transferred into the bone at location 39 beyond which, distally, the implant is smooth. This construction undesirably results in stress shielding. In time, with continued loading of the prosthesis 30, the bone 36 will atrophy, and the patient will experience an even worse condition than the earlier one. However, clinically, there is less thigh pain than with the implant in FIG. 1.

The graduated porosity concept of FIG. 3 enjoys the advantages of FIG. 1 and FIG. 2 without the disadvantages.

Turn now to FIG. 3 which depicts a prosthesis 50 embodying the present invention. The prosthesis 50, which may be termed a substrate, is of metal which would be biologically compatible with both human bone and with soft tissue and would preferably be of stainless steel, or titanium, or alloys of titanium, or alloys of chromium-cobalt. An entire stem 52 extending distally of a shoulder 54 to a distal tip end 56 is porous coated in the manner of the proximal region 28, except that the pore size of the coating is graduated between a proximal region 58 and the tip end 56. Preferably, the porous coating would be metallic and would be of the same material as the substrate, but the materials need not be limited to metals.

In order to load the bone in a more physiological fashion, this invention attempts to force loads into the proximal bone found around a first zone 60 by optimizing bone ingrowth both quantitively and qualitatively into the first zone. The pore size of the first zone 60 ranges between approximately 300 and 400 microns (but not limited to a specific pore size).

In subsequent zones 62, 64, 66 and 68, the pore size is gradually reduced to below a size that can support bone tissue but does allow various soft tissue attachments. More rapid ingrowth will occur at the lower zones where filling a smaller cavity is more rapid than filling a large cavity with bone ingrowth.

Rapid stabilization at zones 64, 66 and 68 by ingrowth will prevent micromotion proximally which causes soft tissue (not bone) ingrowth or tissue inflammation. Bone ingrowth at zones 60, 62 and 64 can thus proceed in the longer time interval required to fill a larger pore diameter.

At zones 66 and 68, the presence of a porous surface enhances the frictional or press fit of the stem to the bone. A smooth surface may allow micro motion, around zones 66 and 68. The presence of tissue attachment to the stem at zones 66 and 68 is thought to be a key factor in reducing tissue irritation caused by the relative motions of bone around a smooth stem present in prior art. Tissue irritation can be a cause of thigh pain present in prior art devices not firmly attached to the bone. The pore size in zones 66 and 68 is smaller than the basic unit of bone, the osteon. An osteon is composed of bone cells surrounding a blood vessel. It is known that bone ingrowth will not occur in pore sizes below approximately 100 microns, the size of an osteon.

From a mechanical point of view, the great differences in stiffness between stem and bone are minimized by the formation of a composite of low stiffness bone, a high stiffness stem and a firmly attached soft tissue intermediary.

With a maximum quantity of bone ingrowth in zone 60 and a minimum of bone ingrowth in zone 68, it is expected that loads will be transferred from the stem maximally in zone 60 and in a decreasing fashion to zone 68. In prior art devices, the loads are transferred from stem to bone in zones 64, 66 and 68 (FIG. 3) with resulting atrophy of bone in zones 60 and 62.

The invention will now be defined more specifically with respect to each of the zones of the stem 52.

In zone 60, the pore size is approximately 325–425 microns. This largest pore size results in a maximum quantity of bone ingrowth resulting in maximum load transfer for maintaining healthier bone. The large diameter pore size also results in large and healthy osteons. Time required for ingrowth are also longer than for that obtained by ingrowth and stabilization at zones 64, 66 and 68.

In zone 62, the pore size is approximately 250–325 microns. This smaller pore size results in a smaller volume or quantity of bone ingrowth. Thus, the amount of ingrown bone at this level is not as voluminous and less bone is available for stress transfer (as in zone 60).

In zone 64, the pore size is approximately 175–250 microns. Smaller bone trabeculi are present in this zone. Areas of soft tissue ingrowth may be present.

In zone 66, the pore size is approximately 100–175 microns. This represents a transition zone with a mixture of bone ingrowth and firm soft tissue attachment.

In zone 68, the pore size is less than approximately 100 microns and supports soft tissue ingrowth only. The rough surface enhances the friction fit of the stem in the femoral canal. Soft tissue ingrowth at this zone can provide substantial attachment, however, being similar to the attachment of a high stiffness tooth to the jaw with Sharpey's membrane. Sharpey's membrane is naturally found in the mouth between and attaching tooth to jaw bone. Many engineers feel Sharpey's membrane represents the ideal material adhering a high modulus (stiff) material (tooth) to a low modulus material (bone). In Zone 68, soft tissue will adhere the stem to the bone in a fashion similar to Sharpey's membrane.

Although the invention is specified for the proximal femur, it has a general application to all types of implants. The purpose of the invention is to maximize bone ingrowth proximally, allow a zone of transition encompassing both bone and fibrous tissue and, distally, permit only tissue ingrowth.

Other advantages include:

(1) Soft Tissue ingrowth distally would overcome the theoretical scenario, wherein bone ingrowth occurs only distally and none proximally, resulting in severe stress shielding of proximal bone;

(2) an implant with fibrous tissue ingrown distally would be theoretically easier to remove, if necessary, than one ingrown with bone;

(3) distal soft tissue ingrowth would result in less thigh pain than a smooth metal stem because there would be less relative motion (i.e., better adherence) than between bone and smooth metal. In the case of a smooth stem implant, no ingrowth or adhesion whatsoever can occur. The natural response to excessive motion is inflammation. By encouraging soft tissue ingrowth into porous metal rather than reactive soft tissue inflammation around smooth metal, the relative motions between the stem and bone are lessened. It is hoped, therefore, that less relative motion will cause less thigh pain.

It is further hoped that research can be performed to identify the "optimal pore size" for various types of fibrous tissues. It is anticipated that optimal soft tissue for ingrowth would be similar at least in function to that of the periodontal membrane (Sharpy's membrane) mentioned above. This includes organized fibrous tissue rather than, for example, synovial tissue or other inflammatory tissues. Future research into "tissue engineering" may identify factors that promote adhesion between soft tissue and implant, with optimum biomechanical properties, such as modulus of elasticity, and load transfer characteristics.

In the most proximal zone 60, a large pore size allows maximum bone volume ingrowth. This by itself tends to negate proximal bone atrophy widely feared with fully porous coated implants. The next zone 62 has a smaller pore size but remains well within the range for bone ingrowth. The next zone 64 optimizes bone ingrowth in a clinically shorter time interval (the larger pore size requires a longer time interval for complete bone incorporation). The next zone 66 simultaneously permits generally equalized amounts of bone and soft tissue ingrowth. The smallest pore size in zone 68 would not enable an osteon (the basic unit of bone in the Haversian system) to occupy that space (below approximately 100 microns), and only fibrous tissue will grow in this zone.

Clinical experience reveals that at transition zones—for example, between porous surface and smooth metal—spot welds (endosteal bridging) are commonly seen. Since, in this invention, many transition zones between different pore sizes are common, it is hoped that more spot welds (endosteal bridging) would occur than with a uniform or only one transition pore size between pores and smooth metal. If on long-term radiographic examination spot welds are indeed seen at these transition points, this could be the basis for a new design incorporating the more frequent transition zones. It is assumed that the transition zones serve as stress risers. The more frequent the stress risers and the more proximal, the more physiological the stress transfer from implant to the bone.

Stress risers may occur at transitions between all zones as load returns to bone from the implant. This is thought to be a positive influence in the design. In fact, if load can be transferred proximally by these stress risers occurring in the region of lines of transition between adjacent zones, this invention will be successful in preventing transfer of load from the implant to the bone at a more distal level. Commonly seen clinically at the junction of porous surface and smooth metal indicated at location 39 is sclerosis of bone indicating transfer of load to bone at that location. Multiple zones of transition may serve to cause sclerosis at more proximal levels, which is more physiological.

In this context, viewing FIG. 4, a load L is depicted being applied to the prosthesis 50 implanted in a femur 70. Arrows 72 serve to indicate transfer of load from the prosthesis 50 to the femur 70 at a transition line 74 between the proximal zone 60 and zone 62. Arrows 76 serve to indicate transfer of load from the prosthesis 50 to the femur 70 at a transition line 78 between the zone 62 and the zone 64. Arrows 80 serve to indicate transfer of load from the prosthesis 50 to the femur 70 at a transition line 82 between the zone 64 and the zone 66. Finally, arrows 84 serve to indicate transfer of load from the prosthesis 50 to the femur 70 at a transition line 86 between the zone 66 and the zone 68.

While a preferred embodiment of the invention has been disclosed in detail, it should be understood by those skilled in the art that various other modifications may be made to the illustrated embodiments without departing from the scope of the invention as described in the specification and defined in the appended claims. The number and location of transition zones are not restricted to the general example of FIG. 3. Future enhancement will likely reveal changes in size and location of porosities and transition zones.

What is claimed is:

1. A surgical prosthetic implant comprising:

a metallic substrate extending between proximal and distal ends for insertion into the cavity of a long bone;

a porous coating on said substrate for encouraging bone and tissue ingrowth comprising at least a layer of particles of metallic material adhered to and extending over substantially the entire surface of said substrate wherein the size of said particles is graduated from a first zone at said proximal end at which said particles have a first predetermined pore size in the range of approximately 325–425 microns to achieve optimal bone-to-implant load transfer, then continuing toward said distal end, through a second zone at which said particles have a second predetermined pore size in the range of approximately 250–325 microns to achieve significant bone ingrowth in a shorter time interval, through a third zone at which said particles have a third predetermined pore size in the range of approximately 175–250 microns to permit some bone ingrowth while also permitting some soft tissue ingrowth; through a fourth zone at which said particles have a fourth predetermined pore size in the range of approximately 100–175 microns for increased soft tissue ingrowth with minimal bone ingrowth; to a fifth zone at which said particles have a fifth predetermined pore size of less than approximately 100 microns for optimal soft tissue ingrowth without permitting bone ingrowth.

2. A surgical prosthetic implant as set forth in claim 1 wherein said particles of said porous coating are of the same material as said substrate; and wherein said coating and said substrate are both biologically compatible with human bone and soft tissue.

3. A surgical prosthetic implant as set forth in claim 1 wherein the metal of said substrate is selected from the group consisting of stainless steel, titanium, titanium alloys, and chromium-cobalt alloys.

4. A surgical prosthetic implant comprising:

a metallic substrate for insertion into the cavity of a long bone, said substrate having a proximal zone, a distal zone distant from said proximal zone, and an intermediate zone between said proximal and distal zones;

a porous coating on said substrate for encouraging bone and soft tissue ingrowth comprising at least a layer of particles of metallic material adhered to and extending over substantially the entire surface of said substrate wherein the size of said particles is graduated from said proximal zone at which said particles are sized for optimal bone-to-implant load transfer, through said intermediate zone at which said particles are sized to permit some bone ingrowth while also permitting some soft tissue ingrowth, to said distal zone at which said particles are sized for optimal soft tissue ingrowth without permitting bone ingrowth.

5. A surgical prosthetic implant as set forth in claim 4 wherein said particles of said porous coating are of the same material as said substrate; and wherein said coating and said substrate are both biologically compatible with human bone and soft tissue.

6. A surgical prosthetic implant as set forth in claim 4 wherein the metal of said substrate is selected from the group consisting of stainless steel, titanium, titanium alloys, and chromium-cobalt alloys.

7. A surgical prosthetic implant comprising:

a metallic substrate extending between proximal and distal ends for insertion into the cavity of a long bone, said substrate having a proximal zone at said proximal end and a distal zone at said distal end distant from said proximal zone; and a porous coating on said substrate for encouraging bone and tissue ingrowth comprising at least a layer of particles of metallic material adhered to and extending over substantially the entire surface of said substrate wherein the size of said particles is graduated from said first zone at which said particles have one predetermined size range for optimal bone-to-implant load transfer to said distal zone at which said particles have another predetermined size range for optimal soft tissue ingrowth without permitting bone ingrowth.

8. A surgical prosthetic implant as set forth in claim 7 wherein said particles of said porous coating are of the same material as said substrate; and wherein said coating and said substrate are both biologically compatible with human bone and soft tissue.

9. A surgical prosthetic implant as set forth in claim 7 wherein the metal of said substrate is selected from the group consisting of stainless steel, titanium, titanium alloys, and chromium-cobalt alloys.

* * * * *